(12) United States Patent
Schneider et al.

(10) Patent No.: US 8,176,767 B2
(45) Date of Patent: May 15, 2012

(54) EXHAUST GAS SENSOR

(75) Inventors: Jens Schneider, Leonberg (DE); Christoph Zimmermann, Albstadt (DE); Sascha Klett, Oppenweiler (DE)

(73) Assignee: Robert Bosch GmbH, Stuttgart (DE)

( * ) Notice: Subject to any disclaimer, the term of this patent is extended or adjusted under 35 U.S.C. 154(b) by 702 days.

(21) Appl. No.: 12/336,615

(22) Filed: Dec. 17, 2008

(65) Prior Publication Data
US 2009/0217745 A1   Sep. 3, 2009

(30) Foreign Application Priority Data
Feb. 29, 2008   (DE) .......... 10 2008 000 463

(51) Int. Cl.
*G01N 7/00* (2006.01)
(52) U.S. Cl. ..................... 73/23.32
(58) Field of Classification Search .......... None
See application file for complete search history.

(56) References Cited

U.S. PATENT DOCUMENTS

| | | | | |
|---|---|---|---|---|
| 4,323,440 A | * | 4/1982 | Akatsuka | 204/428 |
| 4,357,264 A | * | 11/1982 | Chu | 502/77 |
| 5,744,673 A | * | 4/1998 | Skeels et al. | 585/474 |
| 6,276,191 B1 | * | 8/2001 | Schneider et al. | 73/23.31 |
| 7,294,252 B2 | * | 11/2007 | Wang et al. | 205/781 |
| 2001/0022961 A1 | * | 9/2001 | Lee et al. | 423/718 |
| 2003/0092562 A1 | * | 5/2003 | Nakanishi et al. | 502/65 |
| 2007/0017852 A1 | * | 1/2007 | Meyer et al. | 208/213 |
| 2009/0218220 A1 | * | 9/2009 | Matter et al. | 204/424 |

FOREIGN PATENT DOCUMENTS
DE   200 04 514   8/2001
* cited by examiner

*Primary Examiner* — Robert R Raevis
(74) *Attorney, Agent, or Firm* — Kenyon & Kenyon LLP

(57) ABSTRACT

Exhaust-gas sensors that have a sensor element, which is surrounded by two protective tubes on a side facing the exhaust gas and which is additionally protected by a porous fiber package, are already known. The fiber package is disposed between the two protective tubes and is meant to protect the sensor element from thermal shock by water droplets hitting the sensor element. When the exhaust gas sensor is used as primary catalytic converter or raw emission sensor, the sensor element can get damaged by sulfur compounds contained in the exhaust gas. In the exhaust-gas sensor according to the invention, damage to the sensor element by exhaust-gas components contained in the exhaust gas is reliably prevented. According to the invention, the adsorption means is implemented in such a way that sulfur, phosphorus or silicon compounds are trapped irreversibly.

10 Claims, 1 Drawing Sheet

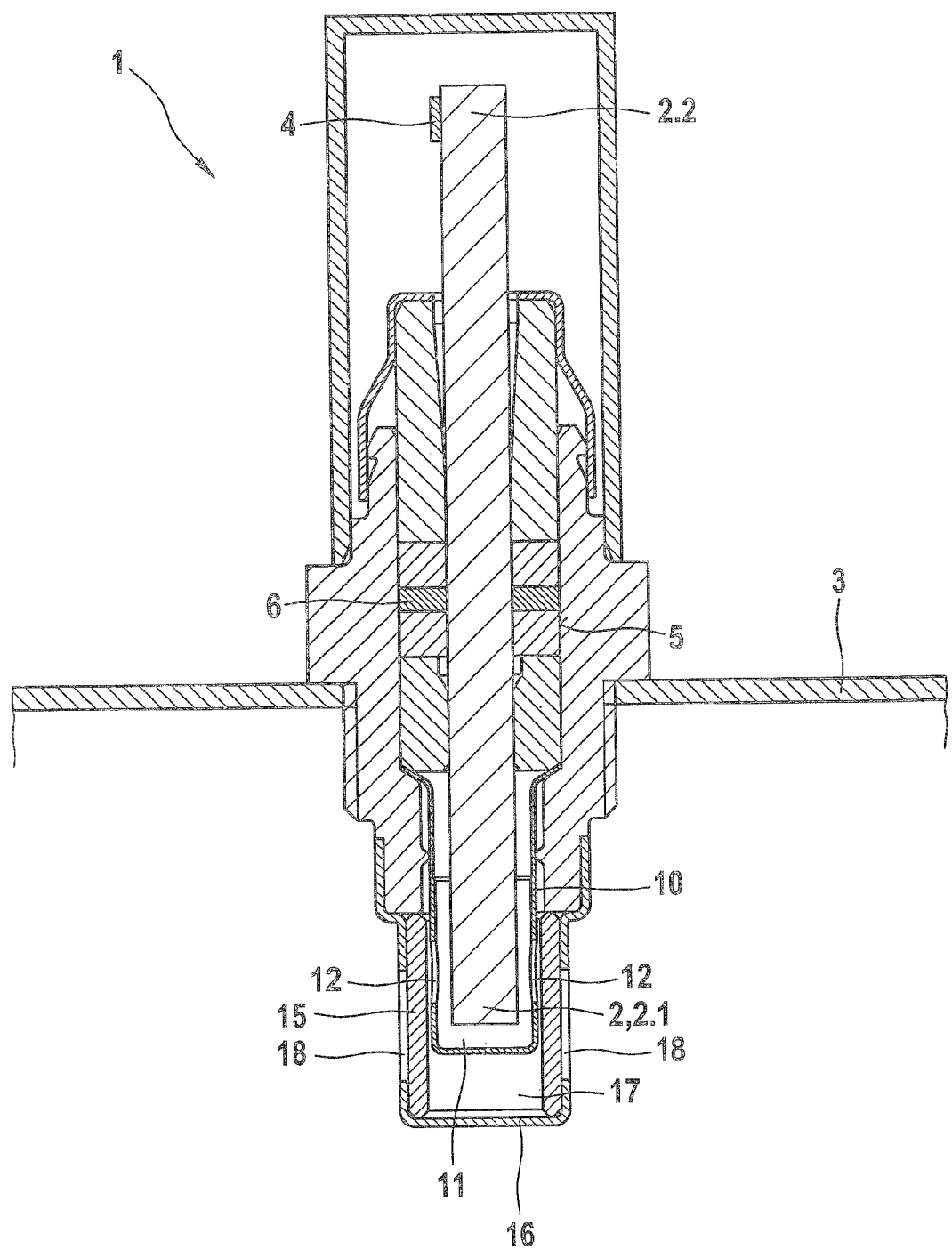

EXHAUST GAS SENSOR

BACKGROUND INFORMATION

An exhaust gas sensor with a sensor element that is surrounded by two protective tubes on a side facing the exhaust gas and which is additionally protected by a porous fiber package is described in German Patent No. DE 200 04 514. The fiber package is disposed between the two protective tubes and is meant to protect the sensor element from thermal shock by water droplets hitting the sensor element. In particular if the exhaust gas sensor is used as primary catalytic converter or raw emission sensor, the sensor element can get damaged by sulfur compounds contained in the exhaust gas.

SUMMARY OF THE INVENTION

The exhaust gas sensor of the present invention has the advantage that damage to the sensor element caused by exhaust gas components contained in the exhaust gas is reliably prevented in that the adsorption means is designed in such a way that sulfur, phosphorus or silicon compounds are adsorbed in an irreversible manner. This traps the harmful substances in the adsorption means, so that they are unable to reach the sensor element.

According to one advantageous embodiment, the adsorption means takes the form of a powder package, pellet package or molded body; the molded body can be a sintered metal body or a porous ceramic body.

It is especially advantageous that the adsorption means includes a means which absorbs sulfur, phosphorus and/or silicon compounds, since the substances contained in the exhaust gas are thus able to be reliably bound in the cavities of the adsorption means by chemical adsorption. The cavities of the adsorption means are designed such that a specified quantity of harmful substances is able to be adsorbed, e.g., a quantity that corresponds to the service life of the sensor.

According to one advantageous development, the adsorption means contains aluminum oxide, at least one oxide or carbonate of at least one of the metals of magnesium, calcium, strontium or barium and/or cerium oxide and/or one or a plurality of the metals of the platinum group of palladium, platinum, rhodium, iridium, ruthenium, in finely dispersed form.

It is very advantageous if the adsorption means is provided in a storage housing which encloses the at least one protective tube, since the absorption means may thus be situated upstream from the sensor element and protected from mechanical loads. For instance, the storage housing is connected to the housing of the exhaust gas sensor or the at least one protective tube in a detachable manner.

BRIEF DESCRIPTION OF THE DRAWING

The FIGURE shows an exhaust gas sensor according to the present invention.

DETAILED DESCRIPTION

The exhaust gas sensor is used, for example, to determine the oxygen concentration in an exhaust gas of an internal combustion engine. However, the exhaust gas sensor may expressly be utilized to determine other physical variables of any other gas as well.

The exhaust gas sensor has a housing 1, inside which a ceramic sensor element 2 is provided with whose aid the physical variable of the measuring gas to be measured is able to be determined. One section of sensor element 2 of the exhaust gas sensor projects into an exhaust pipe 3 of an internal combustion engine.

Sensor element 2 has a section 2.1 on the exhaust-gas side, and a section 2.2 on the connection side, the exhaust-gas side section 2.1 being exposed to the exhaust gas, and the connection-side section 2.2 providing the electrical connection contacts 4 for deriving the measuring signals of sensor element 2.

Housing 1 has a sensor-element channel 5, inside which at least a section of sensor element 2 is disposed and supported. According to the exemplary embodiment, at least one temperature-resistant sealing element 6 is provided in sensor-element channel 5, which seals sensor-element channel 5 from the exhaust gas. Sensor element 2 projects from sensor-element channel 5 by the exhaust-gas-side section 2.1 of sensor element 2 in the direction of exhaust-gas pipe 3.

Exhaust-gas-side section 2.1 of sensor element 2 is surrounded by at least one protective tube 10. The at least one protective tube 10 protects sensor element 2 from liquid droplets contained in the exhaust gas, which mostly form right after an engine start due to condensation, and can cause damage to sensor element 2 as a result of thermal shock when hitting heated sensor element 2. The thermal shock is caused by the evaporation of the water droplet on heated sensor element 2, which causes a locally high temperature gradient that can lead to a tear in the ceramic of sensor element 2. The at least one protective tube 10 is affixed on housing 1 and encloses an interior chamber 11 which accommodates exhaust-gas-side section 2.1 of sensor element 2. Protective tube 10 has the shape of, for instance, a cap, cylinder, cup, cone section or a similar design, for example. The at least one protective tube 10 is provided with passages 12, which allow exhaust gas to flow from exhaust-gas pipe 3 into interior chamber 11 of protective tube 10, and to flow out of interior chamber 11.

In addition, a porous adsorption means 15 is provided, which protects sensor element 2 from harmful exhaust-gas components, such as sulfur, phosphorus or silicon compounds, for instance. Harmful phosphorus compounds are gaseous ($SO_2$, $SO_3$, $H_2S$) or solid sulfur compounds. Harmful phosphorus compounds are, for example, $P_2O_5$ as well as inert, particulate Ca-, Zn-, Fe-phosphates of burned engine oil. Among the harmful silicon compounds are siloxanes or silicates of burned engine oil.

In the reactive, gaseous compounds, the damage takes place via chemical absorption and reaction with the electrode materials, and in the inert particulate exhaust-gas components, the damage takes place by deposition in the pores of protective layers, which usually have a very limited absorption capacity.

The exhaust-gas components named above may lead to the following typical damage and contamination of protective layers and electrodes of sensor element 2:

a) Damage to the NOx trap or electrode material in NOx sensors; $CaCO_3$, $SrCO_3$, $BaCO_3$, for example, react irreversibly with acid sulfur oxides in ambient oxygen, to the corresponding sulfates and lose their effectiveness.

b) Damage to the electrode and protective layers in Lambda sensors and gas-selective exhaust-gas sensors by glazing over; given corresponding temperatures, for instance, sealing and gas-impermeable phosphate glazes form on surfaces containing alkali or earth alkalis.

c) Damage to the catalytically active platinum metal electrodes in lambda sensors and gas-selective exhaust-gas sensors due to Si-contamination; Pd, Pt, Rh-electrodes, for instance, but also mixed electrodes are effectively rendered passive by Si-compounds, i.e., are reduced in their catalytic activity.

According to the present invention, adsorption means 15 is implemented in such a way that sulfur, phosphorus or silicon compounds are able to be irreversibly trapped in cavities of adsorption means 15. Since the sulfur, phosphorus or silicon compounds remain in the material of adsorption means 15 according to the present invention, the afore-described sensor damage is avoided. The trapping or adsorption of the harmful exhaust-gas components takes place by chemical adsorption and/or intercalation. The cavities of adsorption means 15 are designed such that a specified quantity of harmful substances is able to be adsorbed, e.g., a quantity that corresponds to the service life of the sensor.

Adsorption means 15 may be implemented in the form of a loose powder package, loose pellet package, or a solid molded body as in the exemplary embodiment. The molded body may in turn be a sintered metal body or a ceramic body. The molded body is implemented as, for example, hollow cylinder and surrounds protective tube 10.

Adsorption means 15 includes a means for the adsorption of sulfur, phosphorus or silicon compounds, which contains, for instance, aluminum oxide, at least one oxide or carbonate of one of the metals of magnesium, calcium, strontium or barium and/or cerium oxide and/or one or more of the metals of the platinum group palladium, platinum, rhodium, iridium, ruthenium. The metal from the platinum group in adsorption means 15 is present in finely dispersed form. The adsorbent means may contain 50 to 85 vol. % aluminum oxide, and also 15 to 50 vol. % magnesium, calcium, strontium or barium oxide or carbonate, as well as 0 to 10 vol. % cerium oxide and also maximally 0.5 vol. % palladium, platinum, rhodium, iridium, ruthenium. The absorbent means is provided, for example, in the form of an adsorbing layer on the surface of the cavities of adsorption means 15.

Adsorption means 15 is accommodated in a storage housing 16, which also functions as protective tube. A storage chamber 17 inside which adsorption means 15 is disposed is formed between storage housing 16 and protective tube 10. Storage housing 16 is fixedly or detachably connected to housing 1 of the exhaust-gas sensor, for instance with the aid of a welding or screw connection.

In the same way as protective tube 10, storage housing 16 has passages 18 as well, which allow exhaust gas to flow from exhaust-gas pipe 3 into storage chamber 17, and to flow out of storage chamber 17 back into exhaust-gas pipe 3. Storage housing 16 has a cylindrical, hexagonal or oval design, for example, and passages 18 may be disposed on the circumference and/or the end face.

Storage chamber 17 and interior chamber 11 containing sensor element 2 are connected via passages 12 for the flow of fluid, adsorption means 15 being disposed inside storage chamber 17 in such a way that the flow reaches interior chamber 11 essentially only via adsorption means 15. When the flow travels through or across storage means 15, the harmful exhaust-gas components are chemically absorbed from the exhaust gas by the absorbent means and thereby irreversibly trapped by adsorption means 15.

Storage housing 16 is designed in such a way, for instance, that adsorption means 15 is able to be exchanged. To this end, storage housing 16 is detachably connected to sensor housing 1, so that only adsorption means 15 and not the entire sensor has to be exchanged during servicing. For example, storage housing 16 is screw-fitted with sensor housing 1.

What is claimed is:

1. An exhaust-gas sensor comprising:
    a sensor element;
    at least one protective tube surrounding the sensor element on a side facing exhaust gas; and
    a porous adsorption element surrounding the at least one protective tube for protecting the sensor element, the porous adsorption element being configured in such a way that sulfur, phosphorus or silicon compounds are trapped in an irreversible manner.

2. The exhaust-gas sensor according to claim 1, wherein the adsorption element includes a powder package, a pellet package or a molded body.

3. The exhaust-gas sensor according to claim 2, wherein the molded body is a sintered metal body or a ceramic body.

4. The exhaust-gas sensor according to claim 1, wherein the adsorption element absorbs sulfur, phosphorus or silicon compounds.

5. The exhaust-gas sensor according to claim 4, wherein the adsorption element contains aluminum oxide, magnesium oxide or carbonate, calcium oxide or carbonate, strontium oxide or carbonate, barium oxide or carbonate, and/or cerium oxide and/or palladium, platinum, rhodium, iridium, ruthenium.

6. The exhaust-gas sensor according to claim 5, wherein the adsorption element includes 50 to 85 vol. % aluminum oxide.

7. The exhaust-gas sensor according to claim 5, wherein the adsorption element contains 15 to 50 vol. % magnesium oxide or carbonate, calcium oxide or carbonate, strontium oxide or carbonate, barium oxide or carbonate.

8. The exhaust-gas sensor according to claim 5, wherein the adsorption element contains 0 to 10 vol. % cerium oxide.

9. The exhaust-gas sensor according to claim 5, wherein the adsorption element contains maximally 0.5 vol. % palladium, platinum, rhodium, iridium, ruthenium.

10. The exhaust-gas sensor according to claim 5, wherein the adsorption element is situated inside a storage housing, which encloses the at least one protective tube.

* * * * *